US00PP30662P3

(12) United States Plant Patent
Sanderson

(10) Patent No.: US PP30,662 P3
(45) Date of Patent: Jul. 9, 2019

(54) MANDARIN TREE NAMED 'RUBYGS'

(50) Latin Name: *Citrus reticulata*
Varietal Denomination: RubyGS

(71) Applicant: Mildura Fruit Company Trust, Mildura, Victoria (AU)

(72) Inventor: Graeme Sanderson, Dareton (AU)

(73) Assignee: Mildura Fruit Company Trust, Mildura, Victoria (AU)

( * ) Notice: Subject to any disclaimer, the term of this patent is extended or adjusted under 35 U.S.C. 154(b) by 0 days.

(21) Appl. No.: 15/732,223

(22) Filed: Oct. 4, 2017

(65) Prior Publication Data

US 2019/0104662 P1 Apr. 4, 2019

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./202, 201
CPC ..... A01H 5/08; A01H 5/0806; A01H 6/78; A01H 6/785
See application file for complete search history.

(56) References Cited

PUBLICATIONS

Spiegel-Roy et al. Seedless induced mutant in highly seeded lemon (*Citrus* limon) Mutation Breeding Newsletter 36: 10-11, 1990 (Year: 1990).*

Specialty Produce 2018, retrieved on Sep. 10, 2018, retrieved from the Internet at https://www.specialtyproduce.com/produce/Daisy_Tangerines_11860.php, one page. (Year: 2018).*

Barry et al. Daisy Mandarin is self-compatible, *Citrus* Journal 1995 vol. 5, No. 5, one page. (Year: 1995).*

* cited by examiner

*Primary Examiner* — June Hwu
(74) *Attorney, Agent, or Firm* — Michelle Bos Legal LLC

(57) ABSTRACT

'RubyGS' is a new and distinct mandarin tree notable primarily for its reduced number of seeds per fruit as compared to its parent 'Daisy' mandarin. Fruits of 'RubyGS' mandarin are essentially seedless, with less than one seed per fruit on average.

3 Drawing Sheets

Genus and species: *Citrus reticulata.*
Variety denomination: 'RubyGS'.

BACKGROUND AND SUMMARY OF THE VARIETY

The new mandarin tree 'RubyGS' resulted from an induced limb mutation of 'Daisy' mandarin (not patented). Irradiation of 'Daisy' budwood was initially carried out in 1999 at Dareton, New South Wales, Australia using 30 Gy and 40 Gy radiation. Irradiated buds were budded onto seedling rootstocks, and the resulting trees planted in the field in 2001 for observation. Among those was one tree, designated Tree 29, having a limb that produced fruits with an average of 4 seeds per fruit, fewer than were found in fruits on Tree 29 as a whole (average 19 seeds per fruit) and 'Daisy' (average 20 seeds per fruit). Budwood from the selected limb of Tree 29 was budded onto rootstock to produce second-generation trees, which were planted in 2003. Budwood from the second-generation trees was collected in 2006, irradiated at 50 Gy, and budded onto seedling rootstock to create two new trees. One of these trees, designated Tree 29 T2, was chosen for further evaluation, and three topworked trees were established in 2011. Later that year, seven trees were propagated from budwood taken from Tree 29 T2 and the variety was designated 'RubyGS'. 'RubyGS' mandarin tree has been observed and found to retain its distinguishing characteristics through successive asexually propagated generations.

'RubyGS' is a new and distinct mandarin tree notable primarily for its reduced number of seeds per fruit as compared to its parent 'Daisy' mandarin. Fruits of 'RubyGS' mandarin are essentially seedless, with less than one seed per fruit on average, while fruits of 'Daisy' mandarin typically contain 15 to 25 seeds per fruit on average. Similar variety 'Fremont' (not patented) typically contains 16 to 23 seeds per fruit on average. 'RubyGS' has been observed to be sterile under high pollen pressure. 'RubyGS' is further distinguished from 'Daisy' by its later harvest maturity.

BRIEF DESCRIPTION OF THE PHOTOGRAPHS

Figure 1:
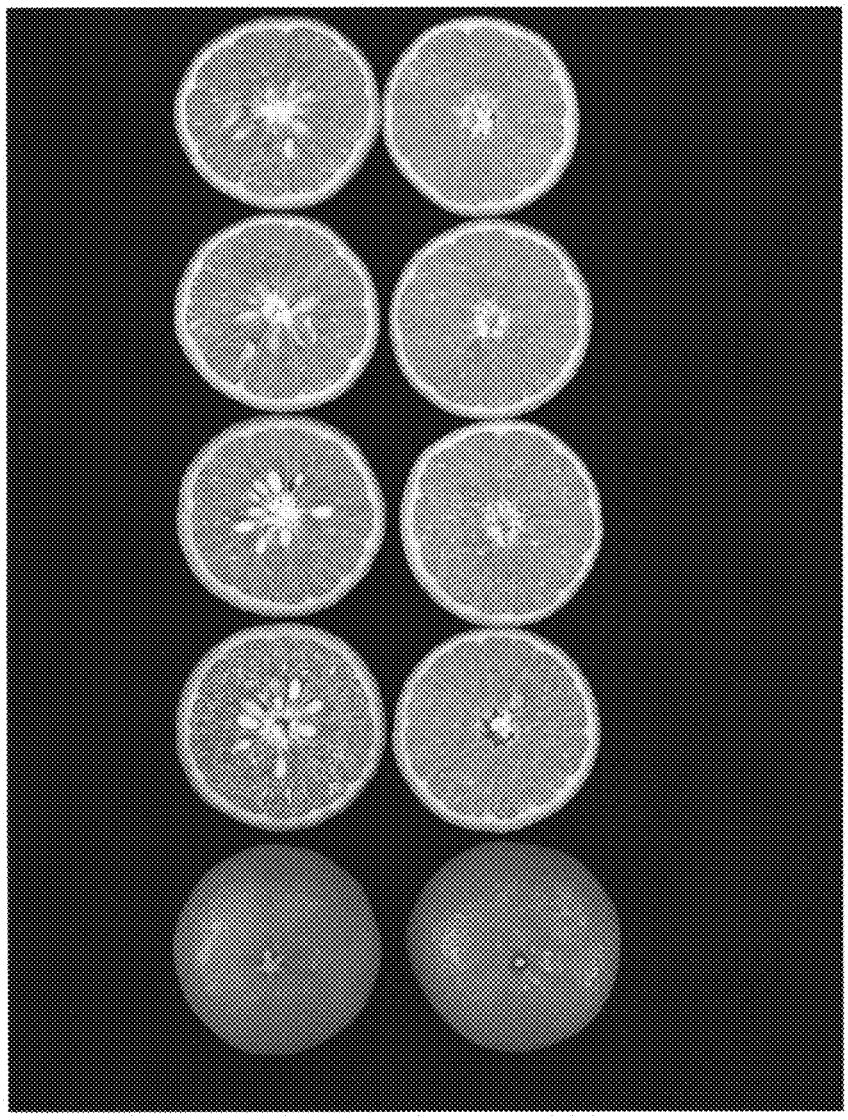
FIG. 1 shows whole and sectioned fruit of 'RubyGS' mandarin.
Figure 2:
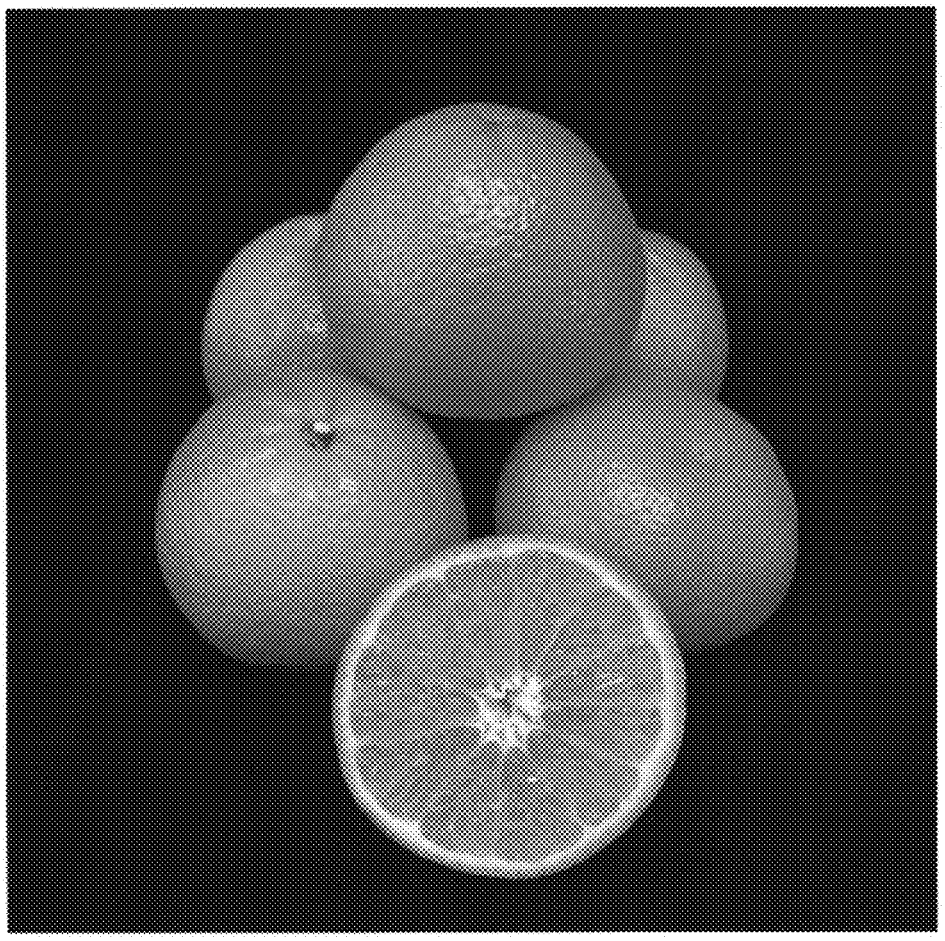
FIG. 2 shows whole and sectioned fruit of 'RubyGS' mandarin.
Figure 3:
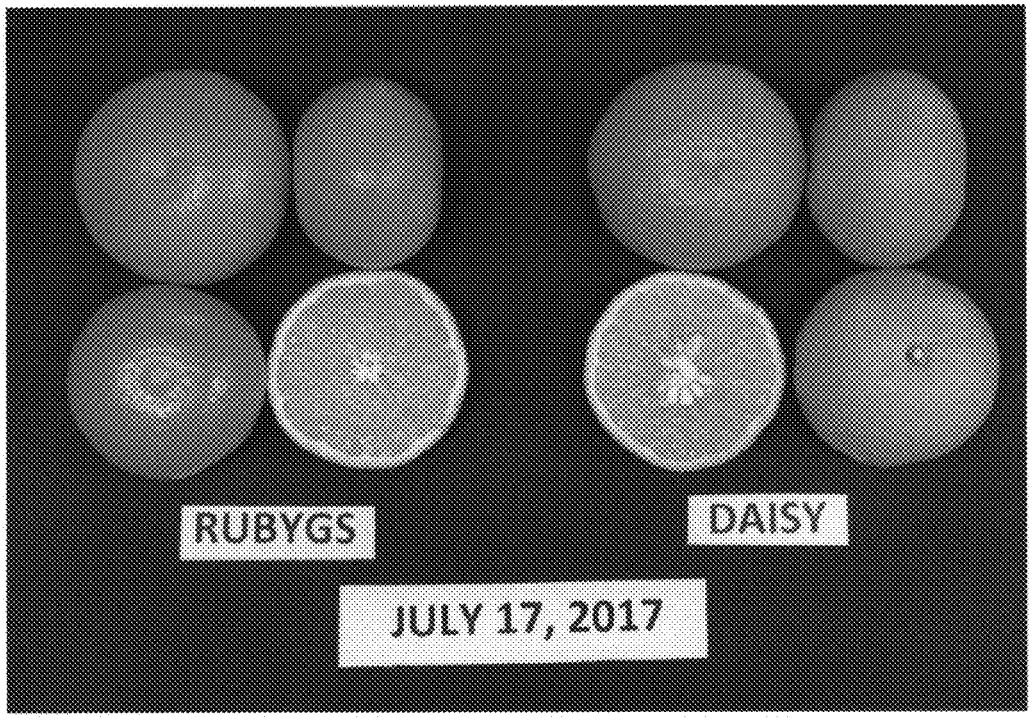
FIG. 3 shows whole and sectioned fruit of 'RubyGS' mandarin and 'Daisy' mandarin.

The attached photographs were taken in 2013 at Dareton, New South Wales, Australia. Actual colors will vary with lighting conditions; color characteristics of 'RubyGS' mandarin should therefore be determined with reference to the observations described herein, rather than from these illustrations alone.

DETAILED BOTANICAL DESCRIPTION

The following detailed botanical description is based on observations made in 2013 of two-year-old 'RubyGS' trees topworked on 'Troyer Citrange' rootstock (not patented) in 2011 at Dareton, New South Wales, Australia. The characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Colors are described with reference to The Royal Horticultural Society Colour Chart (sixth edition).

Tree: Tree size, growth and fruit production characteristics have been evaluated in comparative trials of 'RubyGS' and 'Daisy' for four years at Dareton, Australia. These trials are being replicated at Kenley, Australia.

*Vigor*.—Vigorous; same as 'Daisy'.
*Habit*.—Sprawling and open with first production in second year from planting, becoming more spherical and drooping in subsequent years (similar to 'Daisy').
*Height*.—2.4 m.
*Spread*.—2.3 m.
*Trunk diameter at* 30 *cm above graft*.—62 mm.
*Bark texture*.—Same as 'Daisy'.
*Bark color*.—Greyed-green 197B.
*Alternate bearing*.—Tendency for alternate bearing especially if fruit is held late on the trees (similar to 'Daisy').
*Winter hardiness*.—Winter hardy but not frost tolerant below −2° C. for greater than four hours.
*Chilling requirement*.—Not required but some winter chilling for natural fruit color is advantageous.
*Drought tolerance*.—Not tolerant; typical of *citrus* varieties.

Branch (fruiting branches located about 1 m above graft union):

*Length*.—1.95 m.
*Diameter*.—22 mm.
*Crotch angle*.—40°.
*Bark color*.—Greyed-green 197B.
*Bark texture*.—Smooth to finely raised.
*Thorns*.—Absent.
*Current year shoot length*.—1.6 m.
*Current year shoot color*.—Yellow-green 146C.

Flowers:

*Bud shape*.—Elongated oval.
*Bud length*.—11 mm.
*Bud diameter*.—6 mm.
*Bud color*.—White NN155C.
*Quantity of blossoms per cluster*.—6.
*Blossom diameter*.—24 mm.
*Blossom depth*.—14 mm.
*Fragrance*.—Typical of mandarin varieties.
*Pollen color*.—Strong orange yellow 163B.
*Sepal length*.—2.6 mm.
*Sepal width*.—2.5 mm.
*Sepal shape*.—Same as 'Daisy'.
*Sepal margin*.—Same as 'Daisy'.
*Sepal color*.—Upper surface — Light yellow green 154D.
*Sepal color*.—Lower surface — Light yellow green 154D.
*Quantity of petals per flower*.—5.
*Relative position of petal margins*.—Not touching.
*Petal shape*.—Elongated oval.
*Petal apex*.—Pointed.
*Petal margin*.—Smooth.
*Petal length*.—16 mm.
*Petal width*.—7 mm.
*Petal color*.—Upper surface — White NN155C.
*Petal color*.—Lower surface — White NN155C.
*Date of first bloom*.—Oct. 5, 2017.
*Date of full bloom*.—Oct. 12, 2017.
*Date of first fruitlet fall*.—Oct. 28, 2017.
*Pedicel length*.—6 mm.
*Pedicel diameter*.—1 mm.
*Pedicel color*.—Moderate yellow green 146D.
*Pistil quantity per flower*.—1.
*Pistil length*.—5 mm.
*Pistil color*.—Light yellow green 145D.
*Anther quantity per flower*.—15.
*Anther length*.—7 mm including filament.
*Anther color*.—Moderate yellow 161A.
*Stigma length*.—2 mm.
*Stigma color*.—Strong orange yellow 163B.
*Style length*.—2 to 4 mm.
*Style color*.—Light yellow green 145C.
*Ovary length*.—4 mm.
*Ovary diameter*.—3.4 mm.
*Ovary color*.—Yellow green 144B.
*Self-incompatability*.—Present.

Leaves:

*Length*.—91 mm.
*Width*.—62 mm.
*Blade margin*.—Irregular crenate.
*Leaf shape*.—Elliptic.
*Apex shape*.—Gradually acute.
*Base shape*.—Acute.
*Color of upper surface*.—Green 137B.
*Color of lower surface*.—Yellow-green 146B.
*Texture*.—Upper surface — Smooth.
*Petiole length*.—12 mm.
*Petiole diameter*.—2 mm.
*Petiole color*.—Yellow-green 146B.
*Wings*.—Absent.

Fruit: Fruit of 'RubyGS' has generally the same shape and color characteristics as 'Daisy':

*Quantity per cluster*.—2.
*Axial diameter*.—68 mm.
*Apical diameter*.—37 mm.
*Weight*.—150 g.
*General shape in profile*.—Flattened, circular; truncate at distal end with slight depression.
*Neck*.—Not present.
*Constriction at stalk end*.—None.
*Collar at stalk end*.—None.
*Radial grooves at proximal end*.—Some grooves present, medium length.
*Navel*.—None.
*Areola*.—Not present.
*Rind color*.—Orange-red N30C.
*Color pattern*.—Solid.
*Rind glossiness*.—Medium.
*Oil glands per* $cm^2$.—8.
*Oil gland diameter*.—1.3 mm.

*Rind thickness.*—4.38 mm.
*Ease of peeling.*—Moderate to easy (same as 'Daisy').
*Rind texture.*—Finely textured (same as 'Daisy').
*Albedo color.*—Orange-red N30C.
*Albedo density.*—Medium.
*Albedo thickness.*—2.15 mm.
*Adherence of albedo to flesh.*—Minimal.
*Albedo strands.*—Few to none.
*Quantity of fruit segments.*—11 to 13 (average 12) per fruit.
*Diameter of core.*—Medium.
*Toughness of segment membrane.*—Fine and weak.
*Juice sac length.*—10.25 mm.
*Juice sac shape.*—Ellipse.
*Juice sac length to width ratio.*—3:1.
*Juice sac color.*—Orange N25C.
*Juice soluble solids.*—11° Brix.
*Juice acidity.*—Medium.
*Relative harvest maturity.*—Early.
*Harvest window.*—Mid-season; Mid-July to mid-August (southern hemisphere); about 4 weeks later than 'Daisy'.
*Seeds.*—None (<1 per fruit).
*Stem length.*—6.9 mm.
*Stem diameter.*—4.8 mm.
*Stem color.*—Green 139B.
*Propensity to split.*—None; no evidence of splitting on 2 year old daughter trees.
*Parthenocarpy.*—Present.
*Productivity.*—Two-year-old trees averaged 1.5 kg per tree.
*Market use.*—Fresh market.
*Shipping characteristic.*—Ships very well.
*Storage characteristics.*—Excellent (same as 'Daisy').
*Disease resistance/susceptibility.*—Same as 'Daisy'.

The invention claimed is:

1. A new and distinct variety of mandarin tree, substantially as illustrated and described herein.

* * * * *